(12) United States Patent
Ohishi (10) Patent No.: US 8,463,013 B2
(45) Date of Patent: Jun. 11, 2013

(54) X-RAY DIAGNOSIS APPARATUS AND IMAGE RECONSTRUCTION PROCESSING APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 686 days.

(21) Appl. No.: 12/756,553

(22) Filed: Apr. 8, 2010

(65) Prior Publication Data
US 2010/0260404 A1 Oct. 14, 2010

(30) Foreign Application Priority Data

Apr. 8, 2009 (JP) ................................ 2009-094239
Mar. 17, 2010 (JP) ................................ 2010-060440

(51) Int. Cl.
*G06K 9/00* (2006.01)
*A61B 6/00* (2006.01)

(52) U.S. Cl.
USPC .............................. 382/131; 382/132; 378/4

(58) Field of Classification Search
USPC .......................................... 382/128, 130–132
See application file for complete search history.

(56) References Cited

U.S. PATENT DOCUMENTS

| 7,660,383 | B2 | 2/2010 | Sakaguchi et al. |
| 2004/0175024 | A1* | 9/2004 | Rasche et al. ................. 382/128 |
| 2005/0220264 | A1* | 10/2005 | Homegger ........................ 378/8 |
| 2006/0210019 | A1* | 9/2006 | Rasche et al. ................... 378/62 |
| 2008/0137934 | A1 | 6/2008 | Sakaguchi et al. |

OTHER PUBLICATIONS

U.S. Appl. No. 12/578,862, filed Oct. 14, 2009, Takuya Sakaguchi.

* cited by examiner

*Primary Examiner* — Joseph Burgess
(74) *Attorney, Agent, or Firm* — Oblon, Spivak, McClelland, Maier & Neustadt, L.L.P.

(57) ABSTRACT

According to one embodiment, an X-ray diagnosis apparatus comprises a C-arm, a support mechanism rotatably supporting the C-arm, a rotation driving unit driving rotation of the C-shaped arm, an X-ray tube mounted on the C-arm, an X-ray detector mounted on the C-arm, a control unit controlling the X-ray tube and the X-ray detector, a storage unit storing two-dimensional images generated, a first reconstruction processing unit reconstructing first three-dimensional images respectively corresponding to a plurality of cardiac phases based on acquired two-dimensional images, a positional shift amount calculation unit calculating positional shift amounts respectively corresponding to cardiac phases based on the first three-dimensional images, and a second reconstruction processing unit reconstructing a single second three-dimensional image with a reduced positional shift based on the plurality of acquired two-dimensional images by using the calculated positional shift amounts.

15 Claims, 7 Drawing Sheets

X-RAY DIAGNOSIS APPARATUS AND IMAGE RECONSTRUCTION PROCESSING APPARATUS

CROSS-REFERENCE TO RELATED APPLICATIONS

This application is based upon and claims the benefit of priority from Japanese Patent Applications No. 2009-094239, filed Apr. 8, 2009; and No. 2010-060440, filed Mar. 17, 2010, the entire contents of both of which are incorporated herein by reference.

FIELD

Embodiments described herein relate generally to an X-ray diagnosis apparatus which includes an almost C-shaped arm and can perform rotational imaging, and an image reconstruction processing apparatus.

BACKGROUND

Heart diseases have recently increased in number year by year, and have been the second highest in mortality rate among the Japanese. In many cases of the heart diseases, coronary artery stenoses occur. Stenosis treatment includes surgical operations and interventions. Accidents associated with interventions tend to occur at the stage where a device such as a catheter or guide wire is inserted through a stenotic portion. A doctor is required to comprehend the detailed shape of a stenotic portion during intervention. However, the doctor can only see a contrast-enhanced radiograph during treatment, and there is no means for knowing the detailed structure of the stenotic portion.

There has recently been developed a technique of reconstructing a three-dimensional image based on a plurality of two-dimensional images acquired by rotational imaging.

A coronary artery moves very fast in synchronism with the heart. It is therefore difficult to correct the motion of the coronary artery. The reproducibility of the motion of the heart is low. The position of the heart in a given diastolic phase slightly differs from that in the next diastolic phase. An X-ray computed tomography apparatus acquires data by rotation at a high speed of, for example, 0.4 sec, and hence suffers from only few motion artifacts due to changes in the position of the heart. However, an X-ray diagnosis apparatus cannot rotate at high speed, and hence suffers from relatively many motion artifacts.

Under the circumstances, much attention has been paid to three-dimensional imaging of a coronary artery and stent in the coronary artery. Methods of obtaining such images during intervention include a method of reconstructing images upon two-dimensional motion correction and a method of reconstructing images based on data acquired by executing rotational imaging a plurality of number of times under ECG gated scanning.

In some cases, blood vessel overlapping, shortening, and the like make it difficult to perform two-dimensional motion correction. On the other hand, since ECG gated scanning is performed by executing rotational imaging a plurality of number of times, it takes much time to perform imaging, and increases the amount of contrast medium.

The related art is described in Jpn. Pat. Appln. KOKAI Publication No. 2005-288164.

DETAILED DESCRIPTION

An embodiment of the present invention will be described below with reference to the views of the accompanying drawing.

The following is an outline of a processing procedure in this embodiment.

1) Imaging is repeated while a C-arm is rotated, accompanied by electrocardiographic measurement of an object.

2) A plurality of relatively rough three-dimensional images (3D volume data) respectively corresponding to a plurality of cardiac phases are reconstructed by a iterative reconstruction method.

3) A point in a real space which is anatomically identical to a target point on a relatively rough three-dimensional image is calculated (positional shift calculation).

4-1) A plurality of relatively fine three-dimensional images respectively corresponding to a plurality of cardiac phases are reconstructed by analytic reconstruction processing, accompanied by correction of back projection loci based on positional shifts.

The processing 4-1) described above can be replaced by processing 4-2) and processing 4-3).

4-2) A plurality of relatively fine three-dimensional images respectively corresponding to a plurality of cardiac phases are reconstructed by analytic reconstruction processing.

4-3) A plurality of three-dimensional images shifted based on positional shifts are combined.

The following is an outline of a processing procedure by a modification of this embodiment.

1) Imaging is repeated while the C-arm is rotated, accompanied by electrocardiographic measurement of an object.

2) A plurality of three-dimensional images (3D volume data) respectively corresponding to a plurality of cardiac phases are reconstructed by a iterative reconstruction method or a filtered back projection method.

3) A point in a real space which is anatomically identical to a target point on a three-dimensional image is calculated (positional shift calculation).

4) A plurality of three-dimensional images respectively corresponding to a plurality of cardiac phases are reconstructed by the filtered back projection method.

5) A plurality of three-dimensional images are shifted based on positional shifts.

6) A plurality of combined images are generated by combining a plurality of three-dimensional images while a bias shift pattern is changed. The bias shift pattern is a set of the estimated values of positional shifts corresponding to a plurality of cardiac phases. The estimated values of positional shifts are changed for each of the X-, Y-, and Z-axes pixel by pixel within the range of −3 pixels to +3 pixels. In processing 7) described next, a combined image corresponding to a bias shift pattern substantially exhibiting the minimum positional shift is selected.

7) A combined image exhibiting the minimum positional shift is selected as a final image from a plurality of combined images (fine position correction). A reconstructed image in each cardiac phase comprises a small number of projection data, which cover reconstruction area sparsely. That is, this image is reconstructed from incomplete projection data. The incompleteness of projection data causes artifacts. Artifacts occur on the positive side and the negative side. Positive-side artifacts and negative-side artifacts alternately occur radially from the reconstruction center. The positions where positive-side artifacts and negative-side artifacts appear gradually move due to the influences of the pulsation of the heart. Therefore, the degree of a positional shift appears as the total sum of negative reconstruction values in a combined image. A combined image exhibiting the minimum total sum (absolute value) of negative reconstruction values is selected as a final three-dimensional image exhibiting the minimum positional shift. Reconstruction values may be replaced CT values, the absorption coefficient values, or the absorption coefficient values multiplied a constant coefficient.

Figure 1:
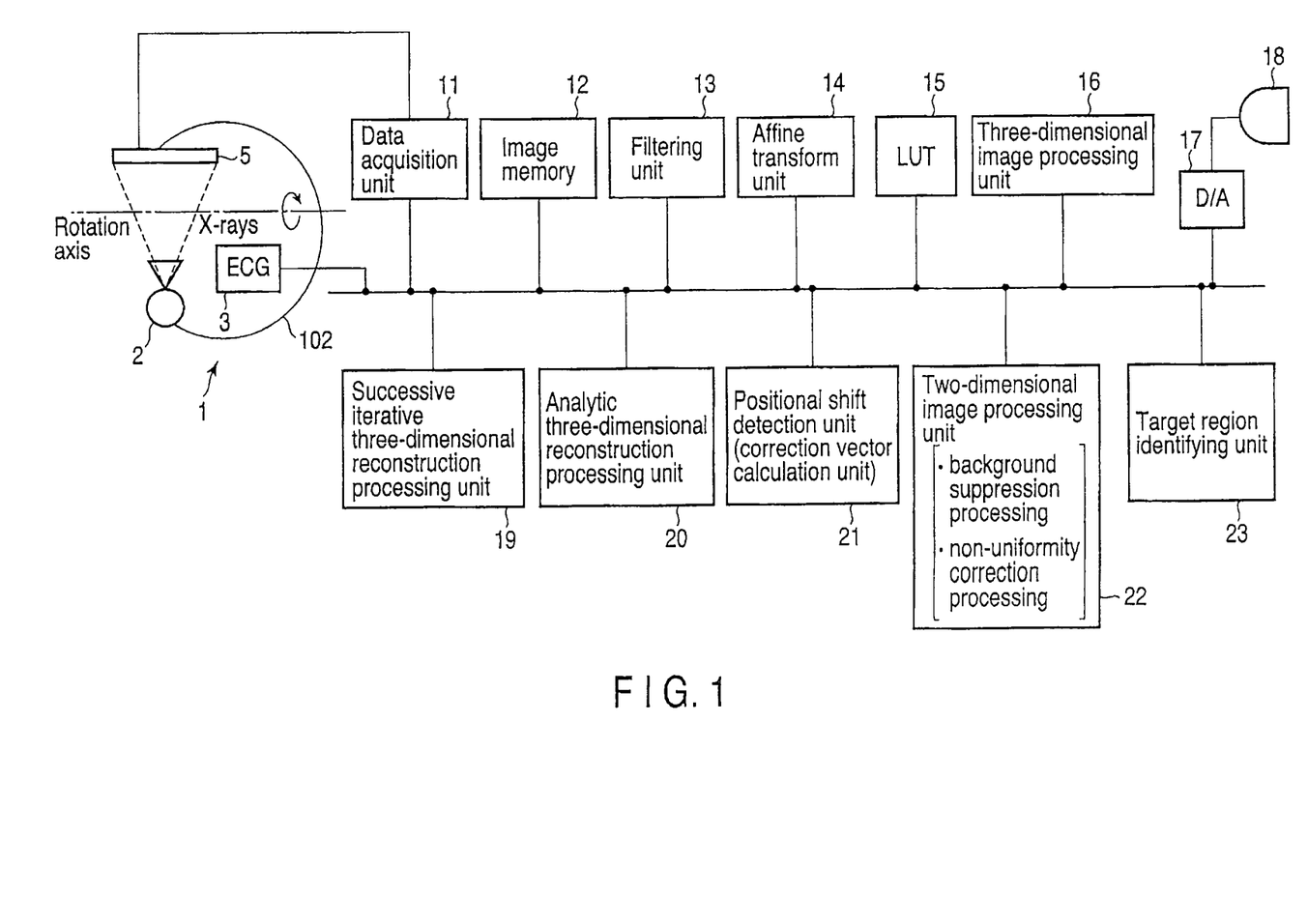
FIG. 1 is a block diagram showing the arrangement of an X-ray diagnosis apparatus according to an embodiment of the present invention.
Figure 2:
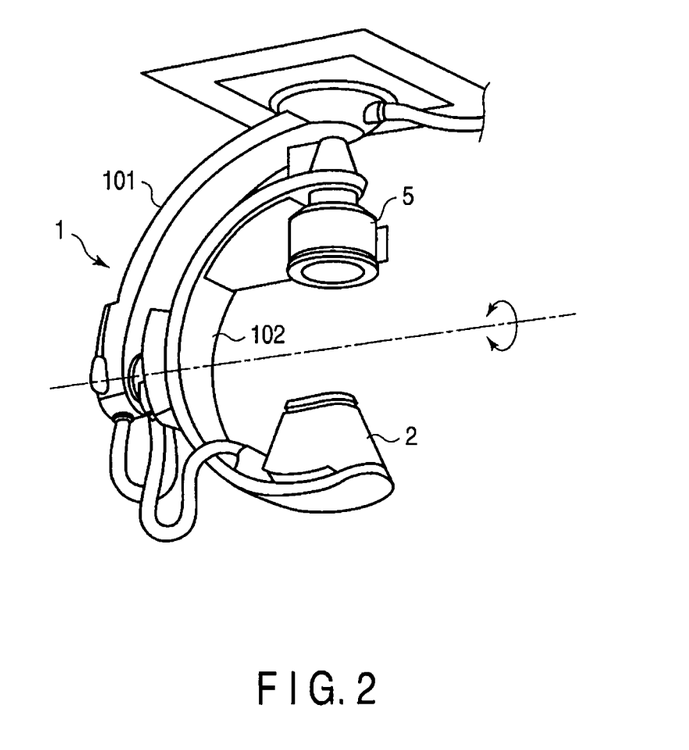
FIG. 2 is a perspective view showing the structure of a gantry in FIG. 1.

As shown in FIGS. 1 and 2, a gantry 1 of an X-ray diagnosis apparatus according to this embodiment includes a C-shaped arm 102 which holds an X-ray tube 2 which generates X-rays in a cone beam shape upon receiving a high voltage from a high voltage generator (not shown), together with a two-dimensional X-ray detector 5 typically serving as an FPD (Flat Panel Detector) which detects X-rays transmitted through an object. A data acquisition unit 11 (not shown) acquires the data of two-dimensional projection images (to be simply referred to as two-dimensional images hereinafter) via the X-ray detector 5. An image memory 12 stores the data of two-dimensional images.

The C-shaped arm 102 forms, together with a hanger arm 101, a support mechanism (not shown). The support mechanism is equipped with an electric motor, and can rotate the C-shaped arm 102 at a constant speed under the control of a control unit. In rotational imaging in step S11 shown in FIG. 3, the C-shaped arm 102 is rotated at a constant speed to continuously generate X-rays, and two-dimensional image data are repeatedly acquired via the data acquisition unit 11 in a predetermined cycle. For example, repeatedly acquiring data at 1° intervals while rotating the C-shaped arm 102 around a patient within the range of an angle of 200° will acquire 200-frame two-dimensional images corresponding to 200° with a view pitch of 1°. The image memory 12 stores the data of a plurality of two-dimensional images acquired by the data acquisition unit 11. The data of a cardiac phase at each imaging operation based on an electrocardiographic waveform from an electrocardiograph (ECG) 3 is associated with each of a plurality of two-dimensional images.

A filtering unit 13 and an affine transform unit 14 perform preprocessing such as high frequency enhancement filtering and image enlargement/movement for two-dimensional images. A lookup table (LUT) 15 converts the tone of an image to be displayed. A three-dimensional image processing unit 16 has a function of converting three-dimensional image data to be displayed into a two-dimensional display image by volume rendering processing including projection processing.

A two-dimensional image processing unit 22 performs subtraction processing for enhancing a contrast-enhanced blood vessel by subtracting two-dimensional images, of the two-dimensional images stored in the image memory 12, which correspond to view angles before and after the injection of a contrast medium, background suppression processing for enhancing a contrast-enhanced blood vessel by using only a contrast-enhanced in the same manner, and density irregularity correction processing. In the background suppression processing in step S12 shown in FIG. 3, for example, an image is generated by applying a low-pass filter to each two-dimensional image, and a corresponding original frame image is subtracted from each filtered image. Note that subtraction may be performed for the data obtained by adding and averaging data corresponding to about one electrocardiographic cycle centered on each frame. In addition, existing background subtraction processing may be applied to the above data.

Figure 3:
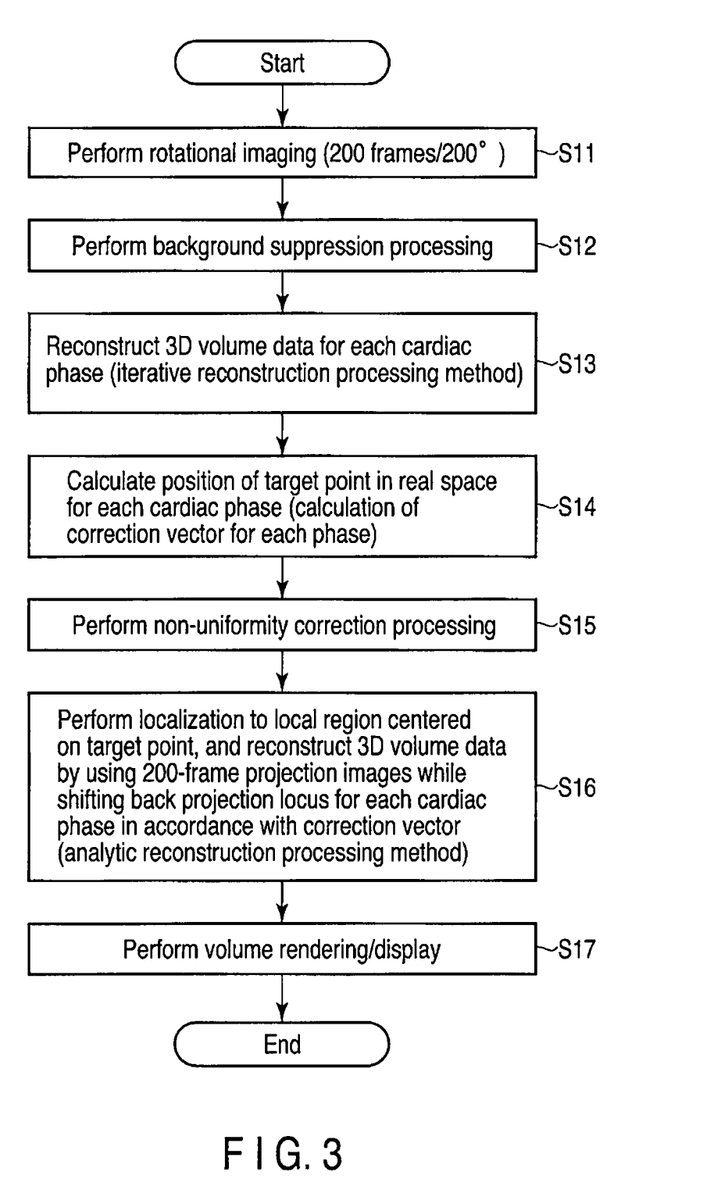
FIG. 3 is a flowchart showing operation in this embodiment.
Figure 4:
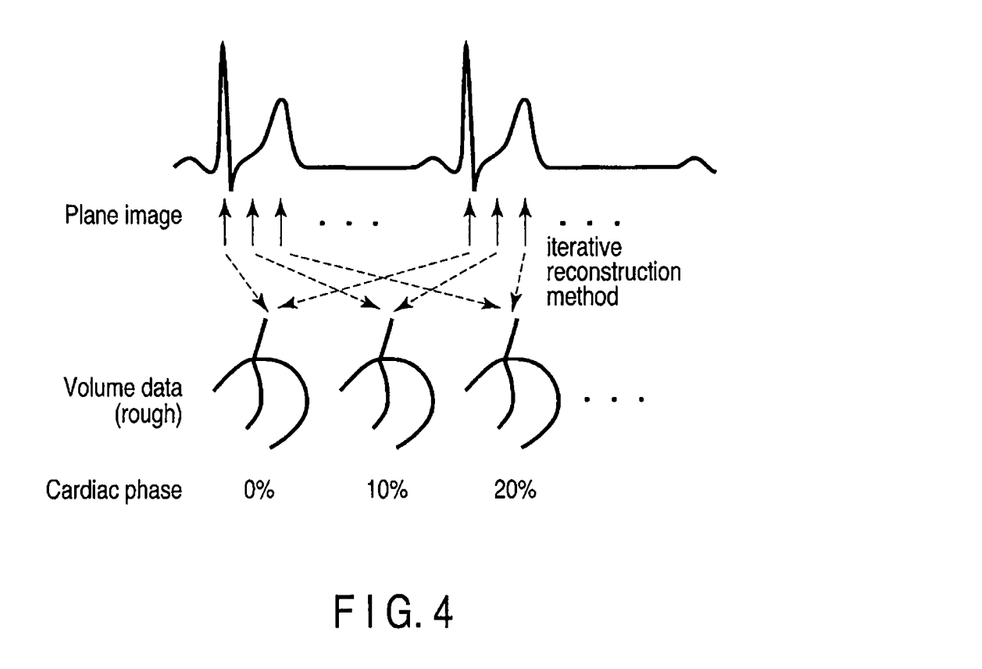
FIG. 4 is a supplementary view for iterative reconstruction processing in step S13 in FIG. 3.

In step S13 shown in FIG. 3, a iterative three-dimensional reconstruction processing unit 19 reconstructs the data of a plurality of relatively rough three-dimensional images (also called volume data) respectively corresponding to a plurality of cardiac phases as shown in FIG. 4 by performing iterative three-dimensional reconstruction processing such as the ART method or MAP-EM method for the overall data acquisition range based on the data of a plurality of two-dimensional images at different view angles (imaging angles) which have undergone background suppression processing. The data acquisition range is defined as a cylinder inscribed in an X-ray beam emitted from the X-ray tube 2 in all directions.

In this embodiment, the iterative three-dimensional reconstruction processing unit 19 reconstructs the data of a plurality of three-dimensional images respectively corresponding to a plurality of cardiac phases.

More specifically, data having undergone background suppression processing is successively approximately optimized according to equation (1) given below:

$$E = |Hf_t - g_t|^2 + |f_t|^2 \quad (1)$$

where H is a projection matrix, $f_t$ is the data obtained by aligning the respective voxels of a reconstructed image in a given cardiac phase t to a column vector, $g_t$ is the data obtained by aligning the projection data having undergone background subtraction processing in the given cardiac phase t to a column vector in the order of the respective pixels and frames, and a is α constant number. Obtaining $f_t$ that minimizes E will complete the reconstruction. This processing is repeated for N cardiac phases t. As a result, the data of N three-dimensional images are generated. Although a method with a noise suppression effect (equation 1) has been described as a reconstruction method, the present invention is not limited to this. It is possible to use other iterative reconstruction methods (e.g., MAP-EM and TV).

In step S14 in FIG. 3, a positional shift detection unit 21 specifies a position (three-dimensional coordinates) in a real space which is anatomically identical to a region (target point) from each of a plurality of relatively rough three-dimensional images which are reconstructed by the iterative three-dimensional reconstruction processing unit 19 and respectively correspond to a plurality of cardiac phases. One of a plurality of specified target points is set as a reference position, and correction vectors associated with N−1 target points are calculated with reference to the reference position.

Figure 6:
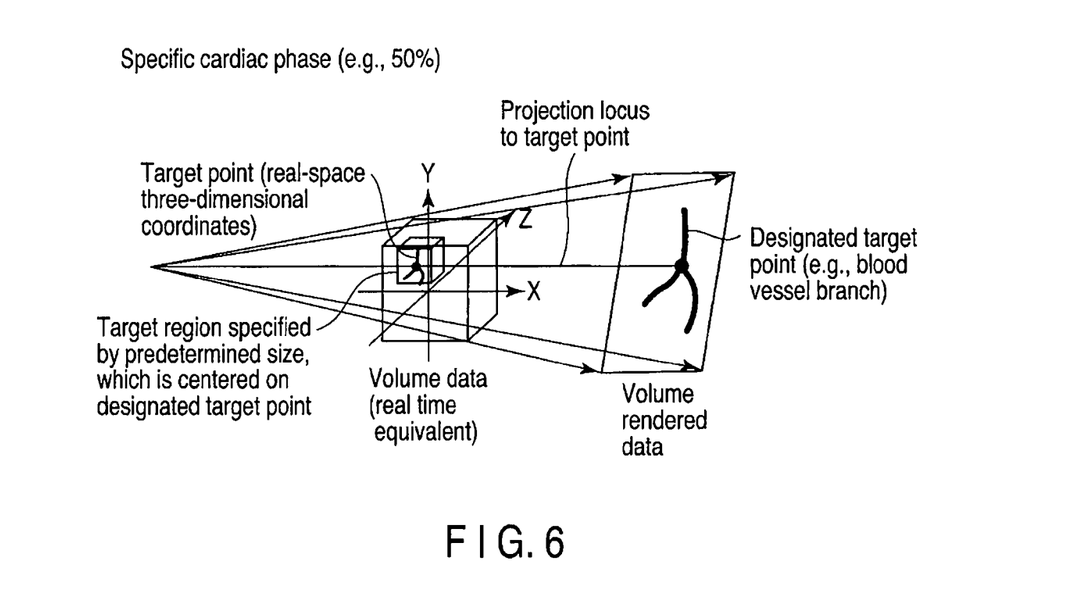
FIG. 6 is a supplementary view for calculation processing for a target point in a specific cardiac phase in target point calculation processing in step S14 in FIG. 3.

In practice, as shown in FIG. 6, a three-dimensional image (reference image) in a predetermined one cardiac phase is selected from N reconstructed three-dimensional images. The three-dimensional image processing unit 16 performs volume rendering processing for the reference image. A display unit 18 displays the volume-rendered image. The operator designates the center (target point) of a target region with an input device such as a mouse (not shown). Typically, a target region is a contrast-enhanced blood vessel, and a target point to be designated is a characteristic region such as a stenotic portion or blood vessel branch portion. The coordinates of the designated target point are sent to a target region identifying unit 23. A projection locus in volume rendering processing which corresponds to the target point is specified. The intersection between the projection locus and the contrast-enhanced blood vessel portion is identified. A blood vessel branch in a local range centered on the intersection is specified as an initial target point.

Figure 7:
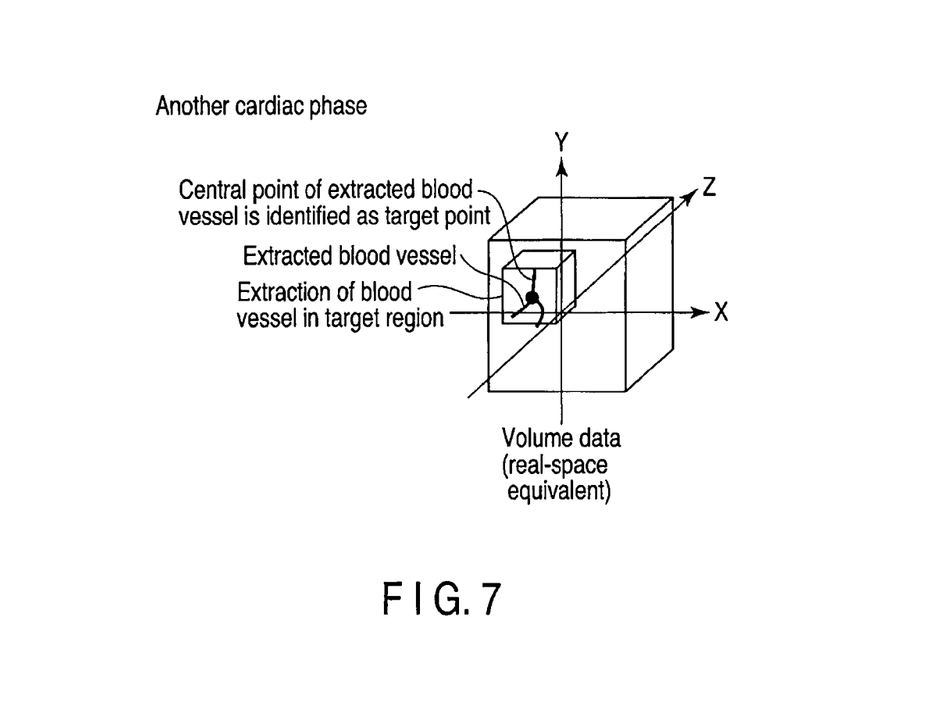
FIG. 7 is a supplementary view for calculation processing for a target point in another cardiac phase in the target point calculation processing in step S14 in FIG. 3.

The data of the N reconstructed three-dimensional images and the coordinate data of the initial target point are sent to the positional shift detection unit 21. As shown in FIG. 7, the positional shift detection unit 21 extracts a target region in the same blood vessel portion by searching for a predetermined range centered on the initial target point on a three-dimensional image in another cardiac phase adjacent to the cardiac phase corresponding to the initial target point, and specifies the center of the extracted target region as a target point in the cardiac phase. The positional shift detection unit 21 repeats this processing in all cardiac phases. The positional shift detection unit 21 specifies a target region with respect to an adjacent cardiac phase in the same manner, and specifies the center of the target region as a new target point in the adjacent cardiac phase. The positional shift detection unit 21 sequentially specifies target points in all the cardiac phases. The positional shift detection unit 21 calculates a correction vector for aligning the coordinates of the target points in all the cardiac phases to the same coordinates. Typically, the positional shift detection unit 21 calculates a correction vector so as to align the coordinates of the target point in another cardiac phase to the coordinates of the target point in the cardiac phase at an middle-diastolic phase.

In step S16 in FIG. 3, an analytic three-dimensional reconstruction processing unit 20 reconstructs relatively fine three-dimensional image data (see FIG. 5) by performing analytic three-dimensional reconstruction processing such as the filtered back projection method, back projection filter method, convolution method, or Fourier transform method based on the data of a plurality of two-dimensional images at different view angles which have undergone subtraction (step S15) of a density irregularity correction image by the two-dimensional image processing unit 22. Density irregularity correction (non-uniformity correction) is performed by subtracting two-dimensional images from air calibration images. The following description is based on the assumption that the filtered back projection method proposed by Feldkamp et al., which can obtain good image quality, is used.

According to the Feldkamp method, first of all, 200 subtraction images are subjected to proper convolution filtering such as Shepp & Logan or Ramachandran. The analytic three-dimensional reconstruction processing unit 20 then shifts a back projection locus in accordance with a correction vector in each cardiac phase. Back projection processing is executed in accordance with the shifted back projection locus. Likewise, the analytic three-dimensional reconstruction processing unit 20 then shifts a back projection locus for each cardiac phase in accordance with a correction vector in a corresponding cardiac phase. The analytic three-dimensional reconstruction processing unit 20 executes back projection processing in accordance with the shifted back projection loci. This reconstructs a three-dimensional image with a reduced positional shift.

Figure 5:
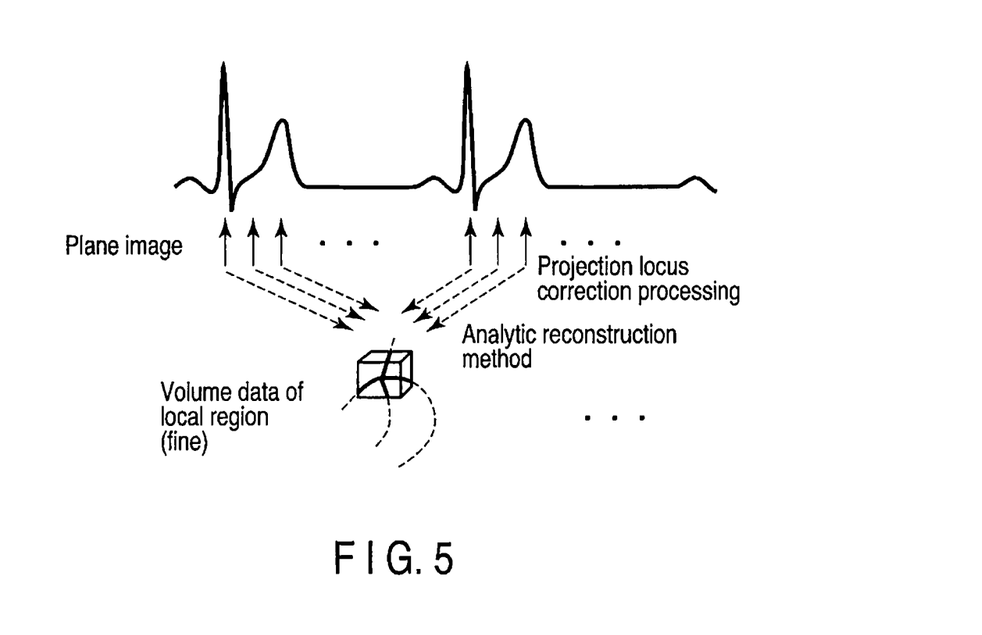
FIG. 5 is a supplementary view for analytic reconstruction processing in step S16 in FIG. 3.
Figure 8:
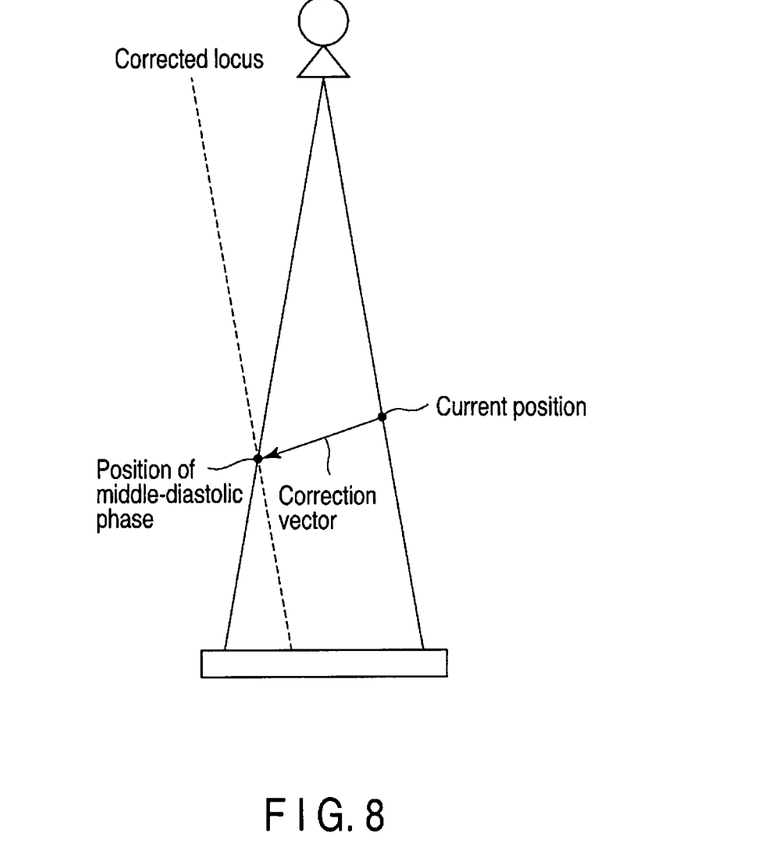
FIG. 8 is a supplementary view associated with locus correction by back projection in the analytic reconstruction processing in step S16 in FIG. 3.

In general, a reconstruction region is defined as a cylinder inscribed in an X-ray beam emitted in all directions. In this case, as shown in FIG. 5, a reconstruction region is a region much narrower than a general reconstruction region centered on the position of a stenotic portion which is designated by the operator. This reconstruction region is preferably a cube of about 3 cm×3 cm×3 cm or a smaller region. When designating a stenotic portion, the operator may designate an approximate range on the portion. Back projection computation is generally performed in accordance with a projection system defined by an X-ray optical system. In this case, however, as shown in FIG. 8, reconstruction is performed upon motion correction by performing back projection computation so as to correct the motion. FIG. 8 shows an example of the reconstruction of the position of a marker. Assume that the position designated by the operator is a diastolic phase, and the current position moves as shown in FIG. 8. Normally, back projection should be performed in accordance with an X-ray locus passing through the current position. However, since the normal position is the position of a diastolic phase, back projection computation is performed such that the locus of the position passes through the same target point and is parallel to a locus passing through the current position. Motion correction is performed in the same manner assuming approximations at positions other than a target point.

Note that a back projection locus is shifted in accordance with a correction vector. However, it is possible to shift each of a plurality of three-dimensional images reconstructed for each cardiac phase in accordance with a correction vector and combine the shifted images.

The three-dimensional image processing unit 16 converts the three-dimensional image reconstructed by the analytic method into an image for display by using a method such as volume rendering. The display unit 18 displays this image.

In the above embodiment, a single point is designated as a target point. However, a plurality of points may be designated. Data within a predetermined range from a designated point is reconstructed and displayed.

In the above embodiment, a target point is designated. However, for example, it is possible to identify a global positional shift upon executing the processing of reducing the resolution while holding branch information and to identify fine positional shift information while sequentially improving the resolution. Performing this processing will eliminate the necessity to designate corresponding points and can reconstruct an overall region at once.

In the above embodiment, a target point is designated. If, however, for example, a device having a GPS function exists near a target region, position correction may be performed based on the information obtained by the GPS function. In this case, since the three-dimensional information of the device can be used, there is no need to perform tracking.

Figure 9:
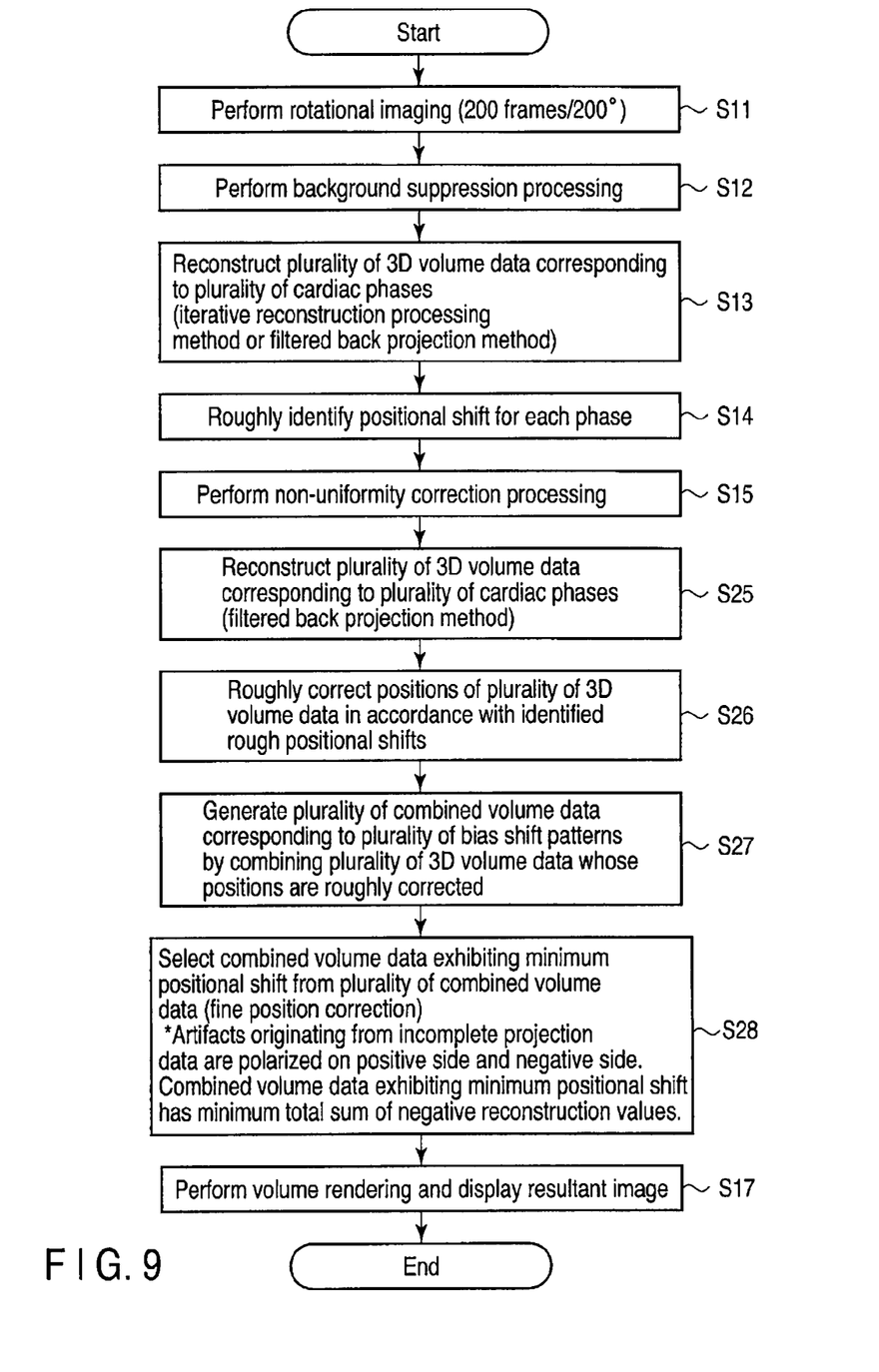
FIG. 9 is a flowchart showing operation by a modification of this embodiment.

FIG. 9 shows a processing procedure by a modification of this embodiment. The same reference numerals as in FIGS. 9 and 3 denote the same steps. First of all, this apparatus repeats imaging during the rotation of the C-arm, accompanied by electrocardiographic measurement of an object (S11). The apparatus then reconstructs a plurality of three-dimensional images (3D volume data) respectively corresponding to a plurality of cardiac phases from a plurality of projection images having undergone background suppression processing (S12) by using the iterative reconstruction method or filtered back projection method (S13), and identifies a positional shift for each phase (S14).

The analytic three-dimensional reconstruction processing unit 20 reconstructs a plurality of three-dimensional images respectively corresponding to the plurality of cardiac phases from the plurality of projection images having undergone density irregularity correction processing (S15) by using the filtered back projection method (S25). The analytic three-dimensional reconstruction processing unit 20 or another position correction processing unit corrects each of the positions of the plurality of three-dimensional images in accordance with the positional shifts identified in step S14 (S26).

The analytic three-dimensional reconstruction processing unit 20 or another position correction processing unit generates a plurality of combined images by repeatedly combining the plurality of corrected three-dimensional images (S27). The plurality of combined images differ in corresponding bias shift patterns. A bias shift pattern is a set of the estimated values of positional shifts relative to a plurality of cardiac phases. The estimated values of positional shifts are changed for each of the X-, Y-, and Z-axes pixel by pixel within, for example, the range of −3 pixels to +3 pixels. Using an enormous number of bias shift patterns will generate an enormous number of combined images with the estimated values of positional shifts being slightly different from each other.

The analytic three-dimensional reconstruction processing unit 20 or another position correction processing unit selects a single combined image exhibiting the minimum positional shift from the enormous number of combined images with the estimated values of the positional shifts being slightly different from each other (S28). With this processing, very fine position correction is performed. A reconstructed image in each cardiac phase comprises a small number of projection data, which cover reconstructuon area sparsely. That is, this image is reconstructed from incomplete projection data. The incompleteness of projection data causes artifacts. Artifacts occur on the positive side and the negative side. Positive-side artifacts and negative-side artifacts alternately occur radially from the reconstruction center. The positions where positive-side artifacts and negative-side artifacts appear gradually move due to the influences of the pulsation of the heart. Therefore, the degree of a positional shift appears as the total sum (absolute value) of negative CT values or image values, that is absorption coefficient multiplied by constant coefficient in a combined image. Negative CT values and negative image values are same in the case of soft-tissue region and air-region, respectively. A combined image exhibiting the minimum total sum of negative reconstruction values is selected as a final three-dimensional image exhibiting the minimum positional shift.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
   a substantially C-shaped arm;
   a support mechanism configured to rotatably support the substantially C-shaped arm;
   a rotation driving unit configured to drive rotation of the substantially C-shaped arm;
   an X-ray tube mounted on the substantially C-shaped arm;
   an X-ray detector mounted on the substantially C-shaped arm so as to face the X-ray tube;
   a control unit configured to control the X-ray tube and the X-ray detector to make the X-ray tube continuously or intermittently generate X-rays during rotation of the substantially C-shaped arm and make the X-ray detector repeat X-ray detection;
   a storage unit configured to store a plurality of two-dimensional images generated under the control of the control unit;
   a first reconstruction processing unit configured to reconstruct a plurality of first three-dimensional images respectively corresponding to a plurality of cardiac phases based on the plurality of acquired two-dimensional images;
   a positional shift amount calculation unit configured to calculate a plurality of positional shift amounts respectively corresponding to the plurality of cardiac phases based on the plurality of first three-dimensional images; and
   a second reconstruction processing unit configured to reconstruct a single second three-dimensional image with a reduced positional shift based on the plurality of acquired two-dimensional images by using the calculated positional shift amounts.

2. The apparatus according to claim 1, wherein the second reconstruction processing unit corrects a position of a projection locus based on the calculated positional shift amount, and reconstructs the second three-dimensional image by analytic reconstruction processing using the corrected projection locus based on the plurality of two-dimensional images.

3. The apparatus according to claim 1, wherein the second reconstruction processing unit reconstructs a plurality of third three-dimensional images respectively corresponding to a plurality of cardiac phases based on the plurality of acquired two-dimensional images, corrects the plurality of third three-dimensional images based on the calculated positional shifts, and reconstructs the second three-dimensional image by combining the plurality of corrected third three-dimensional images.

4. The apparatus according to claim 1, wherein the second reconstruction processing unit reconstructs a plurality of third three-dimensional images respectively corresponding to a plurality of cardiac phases based on the plurality of acquired two-dimensional images, corrects the plurality of third three-dimensional images based on the calculated positional shift amounts, generates a plurality of fourth three-dimensional images by combining the plurality of corrected third three-dimensional images by using a plurality of bias shift patterns, and selects the second three-dimensional image from the plurality of fourth three-dimensional images.

5. The apparatus according to claim 4, wherein the bias shift pattern is a set of estimated values of positional shifts corresponding to a plurality of cardiac phases.

6. The apparatus according to claim 4, wherein the second reconstruction processing unit selects, as the second three-dimensional image, a fourth three-dimensional image exhibiting a minimum total sum of negative reconstruction values from the plurality of fourth three-dimensional images.

7. The apparatus according to claim 1, wherein the positional shift amount calculation unit comprises a volume-rendered image generating unit configured to generate a two-dimensional volume-rendered image with respect to an arbitrary first three-dimensional image among the plurality of first three-dimensional images, an operation unit configured to make an operator perform designating operation for a target point on the volume-rendered image, a coordinate calculation unit configured to calculate real-space three-dimensional coordinates of the target point, a target point specifying unit configured to specify a target point on the same region on each of the first three-dimensional images based on the calculated three-dimensional coordinates, and a storage unit configured to store, as positional shift information, real-space three-dimensional coordinates of a plurality of target points on the plurality of first three-dimensional images.

8. The apparatus according to claim 1, wherein the second reconstruction processing unit reconstructs the second three-dimensional image with respect to a region narrower than a region reconstructed by the first reconstruction processing unit.

9. The apparatus according to claim 1, wherein the first reconstruction processing unit reconstructs the first three-dimensional image by one of a MAP-EM method and an ART method, and the second reconstruction processing unit reconstructs the second three-dimensional image by a filtered back projection method.

10. The apparatus according to claim 1, wherein the first reconstruction processing unit and the second reconstruction processing unit reconstruct the first three-dimensional image and the second three-dimensional image by the filtered back projection method.

11. The apparatus according to claim 1, further comprising a two-dimensional image processing unit configured to suppress backgrounds of the plurality of acquired two-dimensional images.

12. An image reconstruction processing apparatus comprising:
a memory configured to store a plurality of two-dimensional images acquired by rotational imaging; and
a processor storing a program which, when executed by the processor, results in performance of plural program units, comprising,
a first reconstruction processing unit configured to reconstruct a plurality of first three-dimensional images respectively corresponding to a plurality of cardiac phases based on the plurality of acquired two-dimensional images,
a positional shift amount calculation unit configured to calculate a plurality of positional shift amounts respectively corresponding to the plurality of cardiac phases based on the plurality of first three-dimensional images, and
a second reconstruction processing unit configured to reconstruct a single second three-dimensional image with a reduced positional shift by using the calculated positional shift amounts based on the plurality of acquired two-dimensional images.

13. The apparatus according to claim 12, wherein the second reconstruction processing unit corrects a position of a projection locus based on the calculated positional shift amount, and reconstructs the second three-dimensional image by analytic reconstruction processing using the corrected projection locus based on the plurality of two-dimensional images.

14. The apparatus according to claim 12, wherein the second reconstruction processing unit reconstructs a plurality of third three-dimensional images respectively corresponding to a plurality of cardiac phases based on the plurality of acquired two-dimensional images, corrects the plurality of third three-dimensional images by the calculated positional shift amounts, and reconstructs the second three-dimensional image by combining the plurality of corrected third three-dimensional images.

15. The apparatus according to claim 12, wherein the second reconstruction processing unit reconstructs a plurality of third three-dimensional images respectively corresponding to a plurality of cardiac phases based on the plurality of acquired two-dimensional images, corrects the plurality of third three-dimensional images by using the calculated positional shift amounts, reconstructs a plurality of fourth three-dimensional images by combining the plurality of corrected third three-dimensional images by using a plurality of bias shift patterns, and selects the second three-dimensional image from the plurality of fourth three-dimensional images.

* * * * *